United States Patent [19]
Jones

[11] Patent Number: 5,213,965
[45] Date of Patent: May 25, 1993

[54] SOLID-PHASE PRECIPITATION ASSAY DEVICE

[75] Inventor: Ronald M. Jones, Mountain View, Calif.

[73] Assignee: Cholestech Corporation, Hayward, Calif.

[21] Appl. No.: 554,147

[22] Filed: Jul. 16, 1990

[51] Int. Cl.$^5$ .................. C12Q 1/60; G01N 33/92; G01N 21/00

[52] U.S. Cl. .................. 435/11; 436/13; 436/71; 422/55; 422/58; 422/56

[58] Field of Search .............. 435/11; 436/13, 71; 422/55, 58, 56

[56] References Cited

U.S. PATENT DOCUMENTS

| | | | |
|---|---|---|---|
| 3,797,494 | 3/1974 | Zaffaroni | 128/268 |
| 4,144,306 | 3/1979 | Figueras | 422/56 |
| 4,188,188 | 2/1980 | Willner | 23/230 B |
| 4,215,993 | 8/1980 | Sanders | 23/230 |
| 4,477,575 | 10/1984 | Vogel et al. | 436/170 |
| 4,544,630 | 10/1985 | Ziegenhorn et al. | 435/11 |
| 4,826,761 | 5/1989 | Arai et al. | 435/11 |
| 4,987,085 | 1/1991 | Allen | 436/169 |

FOREIGN PATENT DOCUMENTS

| | | |
|---|---|---|
| 1211707 | 9/1986 | Canada . |
| 83113248.5 | 6/1981 | European Pat. Off. . |
| 90116325.3 | 8/1990 | European Pat. Off. . |
| GB88/01044 | 11/1988 | PCT Int'l Appl. . |
| US90/01249 | 3/1990 | PCT Int'l Appl. . |

OTHER PUBLICATIONS

Bachorik, P. S., Methods in Enzymology (1986), vol. 129 "Precipitation Methods for Quantification of Lipoproteins" pp. 78–100, Academic Press, Inc.

*Primary Examiner*—Michael G. Wityshyn
*Assistant Examiner*—Ralph Gitomer
*Attorney, Agent, or Firm*—Peter J. Dehlinger

[57] ABSTRACT

An assay device for measuring the concentration of a soluble analyte, such as HDL-associated cholesterol, in a fluid sample containing interfering compounds, such as LDL-or VLDL-associated cholesterol, which can be selectively precipitated. The device includes a sieving matrix capable of separating soluble and precipitated material migrating through the matrix, and a reservoir which holds a precipitating agent which is effective, within a given concentration range, to selectively precipitate the interfering compounds. The reservoir is designed to delay the release of agent, on contact with the fluid sample, to maintain the concentration of precipitating agent in contact with the fluid sample within the given concentration range.

14 Claims, 5 Drawing Sheets

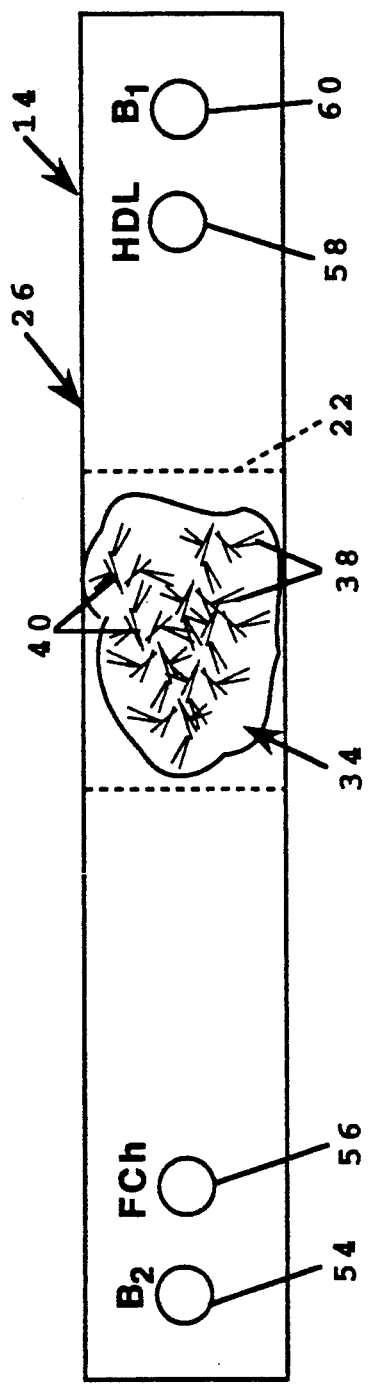
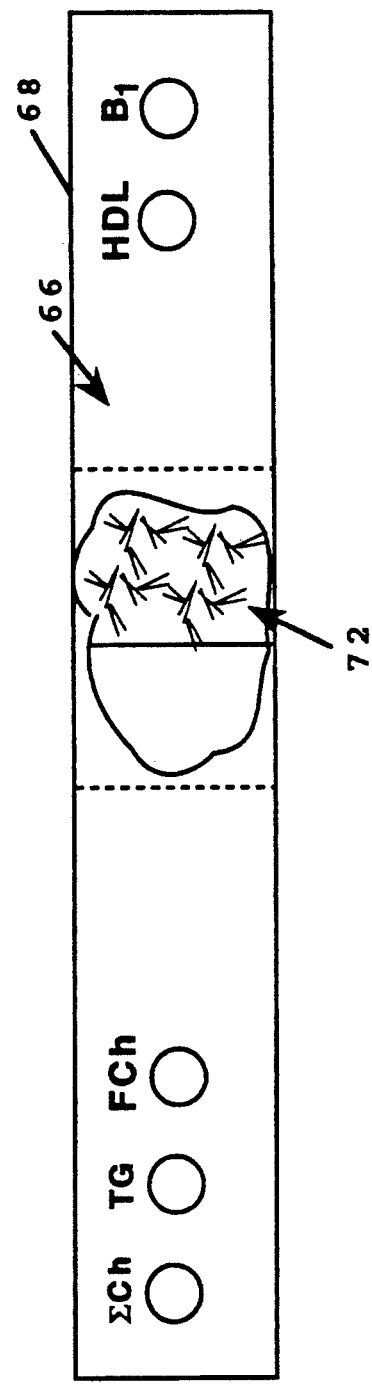
Fig. 6
Fig. 7

SOLID-PHASE PRECIPITATION ASSAY DEVICE

FIELD OF THE INVENTION

The present invention relates to a solid-phase precipitation diagnostic assay device.

BACKGROUND OF THE INVENTION

There is a trend toward widespread testing of blood and other body-fluid analytes which are predictive of health conditions, such as risk of coronary disease. In some assays, such as for determination of serum lipoproteins which are predictive of risk of coronary disease, the analyte of interest, either high-density lipoproteins (HDL) or low-density lipoproteins (LDL), must be separated from other lipoproteins present in the sample fluid.

Considering particularly the case of lipoprotein assays, there are four major classes of lipoproteins found in plasma: chylomicrons, very-low density lipoproteins (VLDL), low-density lipoproteins (LDL) and high-density lipoproteins (HDL). Chylomicrons are large triglyceride-rich particles synthesized in the intestines and serve to transport dietary fats into the circulation. The process of synthesis, secretion, and clearance of chylomicrons from the blood is usually complete within 5–6 hours after a meal, and these particles are usually not detected in serum after a longer period of fasting.

VLDL are triglyceride-rich lipoproteins which are synthesized in the liver and ultimately converted to LDL, which transports most of the plasma cholesterol in humans. HDL is involved in the catabolism of triglyceride-rich lipoproteins, and in the removal of cholesterol from peripheral tissues, and transport to the liver.

Numerous investigations indicate that LDL is an important causative agent of coronary heart disease and other atherogenic conditions, and that high levels of serum cholesterol associated with LDL are indicative of increased risk of atherogenic disease. An inverse relationship between serum HDL levels and risk of coronary disease has also been established. In particular, if the proportion of serum cholesterol associated with HDL is low, the risk of coronary disease is increased.

In view of the importance of HDL and LDL cholesterol levels in the serum to risk management in atherogenic disease, considerable attention has been devoted to testing normal and high-risk individuals for serum levels of HDL, LDL, as well as total cholesterol and triglycerides.

One method for LDL and HDL cholesterol testing is based on the selective precipitation of non-HDL particles in serum by polyanionic compounds, such as dextran sulfate, heparin, and phosphotungstate, in the presence of a group-II cation, such as $Mg^{2+}$, $Mn^{2+}$, and $Ca^{2+}$. The specificity and degree of precipitation are dependent on a variety of factors, including the type and concentration of the polyanion/metal agent. In general, the order of precipitation of serum cholesterol particles, with increasing concentration of polyanion is VLDL, LDL, and HDL. HDL generally remains soluble at concentrations of heparin or dextran sulfate which completely precipitate lower density particles, although minor apoE species of HDL may be coprecipitated with lower density particles.

By selective precipitation of lower density particles, HDL serum cholesterol levels can be determined. The HDL value, along with total serum cholesterol and triglycerides measurements can then be used to calculate LDL according to the relationship:

LDL cholesterol = total cholesterol
- triglycerides/5 - HDL cholesterol.

In a typical lipid assay procedure, a small volume of blood is drawn and centrifuged to produce a clear plasma or serum sample fluid. The sample fluid is then aliquoted into several assay tubes, for determination of (a) total serum cholesterol, (b) triglycerides, and (c) HDL cholesterol. The HDL sample is precipitated, as above, and the lower density particles are removed by filtration or centrifugation prior to cholesterol detection. The samples are then reacted with an enzyme mix containing cholesterol esterase, cholesterol oxidase, peroxidase and a dye which can be oxidized to a distinctly colored product in the presence of $H_2O_2$. The tubes may be read spectrophotometrically, and the desired total, HDL and LDL cholesterol values determined.

Despite the accuracy and reliability which can be achieved with the liquid-phase cholesterol assay just described, the assay has a number of limitations for use in widespread screening. First, the method uses a venous blood sample, requiring a trained technician to draw and fractionate the blood sample, and aliquot the treated blood to individual assay tubes. At least one of the sample tubes (for HDL determination) must be treated with a precipitating agent, and further processed to remove precipitated material. Although some of these procedures can be automated, analytical machines designed for this purpose are expensive and not widely available outside of large hospitals.

SUMMARY OF THE INVENTION

It is one object of the invention to provide an assay device which substantially overcomes or reduces above-mentioned problems associated with liquid-assay procedures for assaying serum LDL, HDL, and total cholesterol values.

A more general object of the invention is to provide an improved solid-phase assay device for measuring a soluble analyte in a fluid sample which also contains a soluble assay-interfering compound.

The assay device of the invention includes a sieving matrix capable of separating soluble from precipitated material in a fluid sample, as the sample flows through the matrix from a sample-application site to a sample-collection site on the matrix. A reagent reservoir in contact with the matrix is designed to slowly release a precipitating agent into the matrix, as fluid sample flows through the matrix. The slow release provides a concentration of precipitating agent in the matrix which is effective to precipitate interfering compound(s) in the sample, without precipitating the analyte being assayed. Also included in the device is an assay pad in which fluid sample collected at a sample-collection site on the matrix is measured.

In one embodiment, the reservoir is composed of a pad or filter impregnated with the precipitating agent which is formulated with a binder for slow dissolution on contact with sample fluid. Alternatively, the precipitating agent may be coated with a slow-release water-soluble coating.

In another embodiment, designed for assaying large macromolecular analytes, the reservoir may be composed of microspheres or microcapsules composed of a size-limited membrane and encapsulated precipitating agent. The membrane allows the precipitating agent to migrate into the matrix, but prevents influx of the analyte and interfering compound(s) from the matrix into the microspheres.

In a device intended for use in measuring serum HDL cholesterol, the precipitating reagent preferably includes a polyanionic compound, such as a sulfated polysaccharide and a group II metal cation, where one or preferably both of the components of the reagent are entrapped in a reservoir for slow release. The final concentration of released reagent in the matrix is effective to selectively precipitate VLDL and LDL particles. The slower migration of the precipitated particles, relative to HDL, serves to separate HDL from other lipoprotein particles at the sample-collection site of the matrix.

These and other objects and features of the invention will become more fully apparent when the following detailed description of the invention is read in conjunction with the accompanying drawings.

BRIEF DESCRIPTION OF THE DRAWINGS

FIG. 6 is a plan view of a strip in the assay device designed for determination of serum cholesterol associated with HDL;

FIG. 7 is a plan view of a strip in the assay device designed for determination of total serum cholesterol, HDL cholesterol, serum triglycerides, and LDL cholesterol.

DETAILED DESCRIPTION OF THE INVENTION

A. Assay Device

Figure 1:
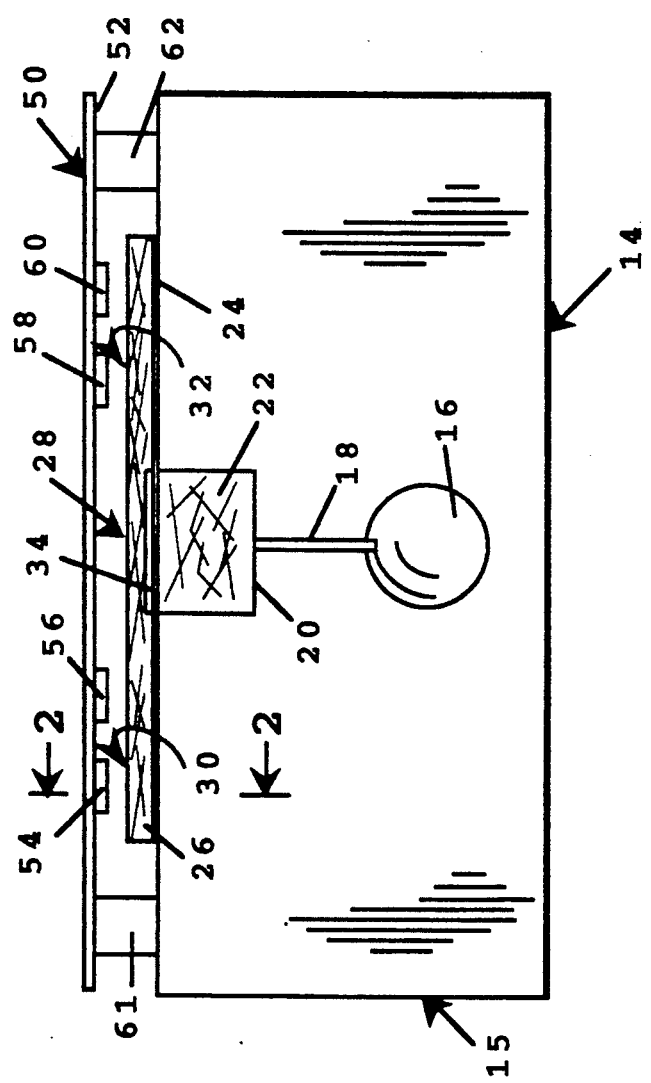
FIG. 1 is a side view of a multi-analyte assay device constructed in accordance with the invention.
Figure 2:
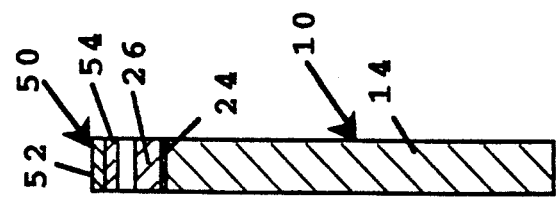
FIG. 2 is a sectional view taken along line 2—2 in FIG. 1.
Figure 3:
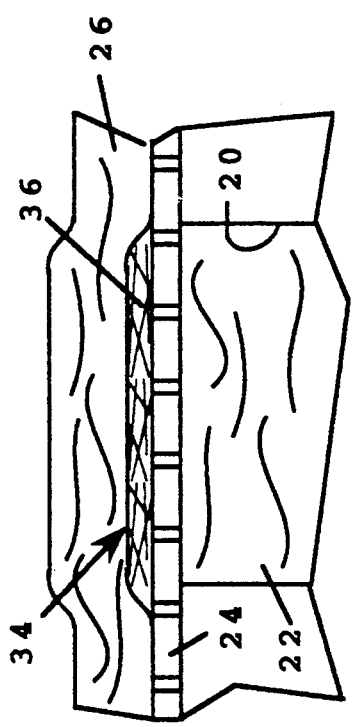
FIG. 3 is an enlarged fragmentary view of the central strip region of the assay device in FIG. 1.

FIGS. 1-3 illustrate a multiple-analyte assay device 14 designed for measuring a soluble analyte in a fluid sample which also contains an interfering compound. The interfering compound may be one which reacts with reagents used for detecting the analyte of interest, inhibits such reagents, or non-specifically interferes with the level of signal produced in the analyte-specific reaction. The interfering compound is also one which can be selectively precipitated (or aggregated) under conditions which do not precipitate the soluble analyte molecule or molecular complex. Selective precipitation is produced by a precipitating agent within a given concentration range. The interfering compound may be incompletely precipitated below the concentration range, and above this range, precipitation of the analyte may occur.

One exemplary analyte for detection by the present invention is high-density lipoproteins (HDL) cholesterol. As discussed above, HDL is one of the classes of lipoproteins which carries cholesterol in the blood, and cholesterol levels associated with HDL, and with low-density lipoproteins (LDL), provides a strong correlation with cardiovascular disease. The interfering compounds in the HDL assay are therefore the non-HDL serum lipoproteins, including chylomicrons, VLDL and LDL. As will be discussed below, the non-HDL lipoproteins can be selectively precipitated by a variety of polyanionic compounds, in combination with group-II metal cations, within selected concentration ranges of the precipitating components.

The assay device described below is designed particularly for determining multiple analytes using a small blood-sample volume, typically between 10-50 $\mu l$ of blood. The general assay configuration has been described in co-owned U.S. patent application Ser. No. 503,311, for Multi-Analyte Assay Device, filed Feb. 15, 1990, and is suitable particularly for determination of multiple blood-sample assays.

Device 14 generally includes a support 15 which defines a well 16 dimensioned and sized to receive a quantity of a blood sample, and typically between about 25-50 $\mu l$ of blood. A capillary conduit 18 formed in the plate is provided at the base of the well and communicates with notched region 20 formed in the upper edge of the support. The construction of the well, tube and notched region in the support can be appreciated from FIGS. 1 and 3. The support is preferably a thin plastic plate or the like, with the well, tube and notched region formed by standard molding or machining methods.

A sieving pad 22 carried in region 20 functions to partially remove blood cells (including blood cells and other large particulate material in the blood sample) as the sample migrates through the matrix in a bottom-to-top direction in the figures. Specifically, pad 22 is formed of a fibrous matrix filter material designed to draw aqueous fluid by surface wetting, and to retard the movement of blood cells as the blood sample is drawn through the matrix. That is, the matrix serves as a chromatographic medium for separating cell-size particles from soluble serum components on the basis of different migration rates through the medium.

A variety of fibrous materials, such as are used in fibrous-mat filters, including cellulose, cellulose acetate, and glass fibrous matrices, are suitable materials for the pad. The fibers may be crosslinked, if desired, by chemical crosslinking, heat fusion, or the like. Also suitable are porous substrates, such as sintered glass, fused polymer beads, and the like whose wettability and dimension of interstices are such as to promote movement of an aqueous medium into the matrix by surface wetting. One exemplary filter is a glass fiber filter, such as a GF/D or PD008 filter supplied by Whatman, having a packing density of about 0.16 $g/cm^3$. The strip is cut to side dimensions of about 3×8 mm, and a thickness of about 1 mm. The pad is dimensioned to absorb a defined volume of sample fluid, typically about 3-25 μl, and preferably between about 15-25 μl.

The upper surface of pad 22 is covered by a microporous membrane 24. This membrane is designed to filter out blood cells and other particulate matter present in the fluid sample. Where the device is used for assaying total cholesterol or other lipid components which may be associated with large lipoprotein bodies in the blood, e.g., HDL, LDL, and VLDL, the membrane pore sizes are selected to filter out blood cells, but allow passage of these lipid bodies. One preferred membrane is a polycarbonate membrane available from Nuclepore (Livermore, Calif.) and having a 1 micron pore size. The membrane is also referred to herein as filter means.

Membrane 24, in turn, is covered by an elongate strip or matrix 26 which is attached to and extends along an interior portion of the plate's upper edge. Matrix 26 serves to distribute sample fluid from a central sample-application region 28 of the strip, which is in contact with pad 22 through membrane 26, to opposite sample-collection regions 30, 32 adjacent the ends of the matrix. The matrix is preferably formed of a fibrous material, such as employed in pad 22, which is capable of drawing fluid through the strip by capillary flow. One exemplary strip material is BSB-20 glass fiber filter available from Whatman having a packing density of about 0.2 gm/cm$^3$, a width of about 3 mm, a length of about 3 cm, and a thickness of about 0.12 mm.

A reagent reservoir 34 in the device contains the precipitating agent used to selectively precipitate the interfering compound(s) in the assay. The reservoir is designed to release the precipitating agent at a rate which maintains the concentration of agent in the sample fluid entering the matrix, and more specifically, at least the first 10% and preferably 20-40% of the total sample fluid which is drawn into the matrix between the sample-application and sample-collection sites on the matrix, within a concentration range which is effective to selectively precipitate or aggregate the interfering compound(s) in the sample fluid.

The precipitating agent is any chemical component or components (a) whose ability to precipitate the interfering compound is concentration dependent, and (b) which is released from the reservoir into the sample fluid in soluble form. The agent may be a salt, producing a salting out precipitation effect, an acid or a base, producing a selective pH-dependent precipitation effect, or more typically, a compound or compounds which forms intermolecular aggregates with the interfering compound(s). Examples of such compounds, for use in selective precipitation of non-HDL particles, are given in Section B below.

With reference to FIG. 3, reservoir 34 includes a fibrous web 36 which is interposed between membrane 24 and the central region of matrix 26. As seen, the web extends somewhat beyond the edges of region 20, ensuring that sample fluid being drawn from pad 22 into matrix 26 is also drawn through the reservoir. The web may be formed of a fibrous filter material such as employed in pad 22 and matrix 26. One exemplary strip material is a glass fiber filter having a packing density of about 4.0 gm/cm$^3$, a thickness of about 0.12 mm, and length and width dimensions of about 4 and 3 mm, respectively.

Figure 3C:
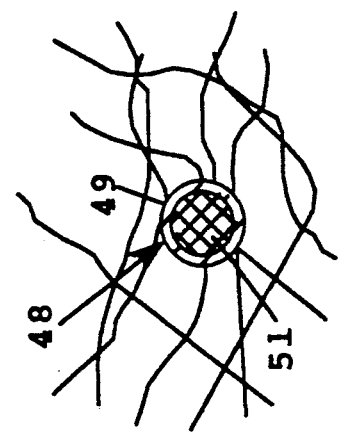
FIGS. 3a-3c are enlarged sectional views of three different types of slow-release reservoirs which may be employed in the FIG. 1 device.
Figure 3B:
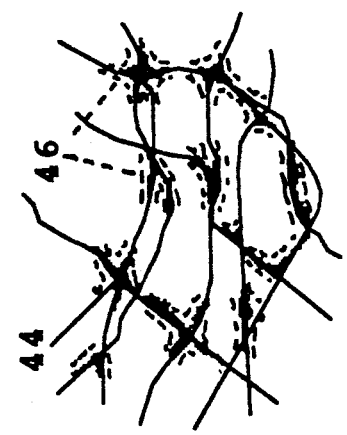
Figure 3A:
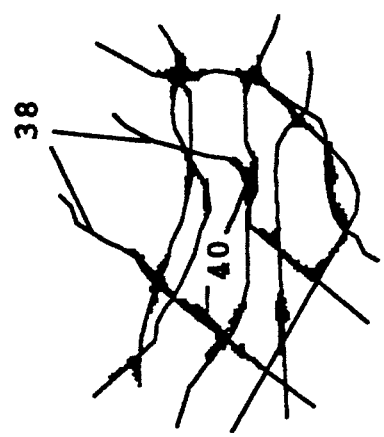

In the embodiment illustrated in FIG. 3a, which shows an enlarged portion of the web, the precipitating agent is formulated in a binder and dried onto the fibers of the web. That is, the fibers of the web, indicated at 38, are encased in a dried irregular deposit 40 of a binder/precipitating agent mix. The binder material and proportion of binder to precipitating agent in the formulation are selected to provide gradual particle dissolution over the period when sample fluid is drawn into the matrix, and more specifically, when the first 10-40% or more of total sample fluid is drawn into the matrix.

Preferred polymer binders are linear polyoxides, polypropylene oxides, polyethylene imines, polyacrylic acid, polyacrylamide, polymethacrylamide, polymethacrylic acid, polyvinylacetate, polyvinylpyrrolidone, polyvinyloxazolidone, and a variety of water-soluble hydroxyl polymers, such as natural gums, gelatin, and water-soluble cellulose compounds, such as methylcellulose and hydroxymethylcellulose, and co-polymers and blends of these polymers). These polymers are generally available commercially in a variety of molecular weight sizes. Binder formulations can be prepared by blending the binder with the precipitating agent, typically in a weight ratio of between about 1:10 to 1:1 precipitating agent:binder.

The dried binder formulation typically contains between about 1:10 1:1 agent:binder, according to nature of the binder and desired dissolution rate of the reservoir. It is noted, however, that the binder itself may be the precipitating agent or one of the components of the agent, such as a dextran sulfate polymer in a precipitating agent composed of dextran sulfate and $Mg^{2+}$.

To prepare the reservoir, the web is infused with a suspension of the binder formulation containing a known quantity of the precipitating agent. The web is then dried, e.g., under vacuum, or by heating, resulting in web coating as shown in FIG. 3a. Example 1 describes the preparation of a reservoir of this type containing dextran sulfate and $MgCl_2$.

In a second embodiment, illustrated in FIG. 3b, the precipitating agent is infused into the web and dehydrated, forming a deposit 44 on the fibers of the web. This deposit is then coated with a water-soluble material, typically a water-soluble polymer such as mentioned above, forming a slow-release coating 46 (shown in dotted lines) on the deposit which acts to delay dissolution of the deposit on contact with sample fluid. The coating may be applied by spraying, dipping, or dehydration from a non-aqueous solvent mixture applied to the web and deposit. The coating is preferably applied so as to achieve different thicknesses of coating throughout the web, to produce a continuum of released agent as sample material flows through the reservoir.

FIG. 3c illustrates a microsphere or microcapsule type of reservoir particle 48 in the reservoir. The microspheres are composed of a microporous polymeric outer shell 49 and an encapsulated interior region 51 which contains the precipitating agent. The microspheres with encapsulated agent are prepared according to known methods, such as described in U.S. Pat. No. 3,797,494 and 3,464,413, and embedded in the web. The porosity of the microspheres is such as to exclude the analyte compound of interest, to prevent exposure of analyte to the high concentration of the precipitating agent within the microspheres.

With continued reference to FIGS. 1 and 2, device 10 includes a test plate 50 composed of an elongate support 52, and multiple wettable, absorbent test pads 54, 56, 58, and 60 carried on the lower surface of the support, at the positions shown. The support is transparent or has transparent windows which allow the pads to be viewed through the support. The pads in the test plate are attached to the support by a transparent or translucent adhesive material, or by sonic welding or other suitable bonding method. Each pad contains analyte-dependent reagents effective to produce an analyte-dependent change in the pad which can be detected optically, either visually or by a detector, in a known manner. The nature of the reagents for exemplary cholesterol and triglyceride assays is given below in Section B. Desirably, the reaction pads are porous, fused polymer or microporous polymer membranes having a thickness, after complete penetration of the fluid, of about 100–150 $\mu$ and side dimensions of about 3 mm. The absorption volume of each pad is preferably between about 0.5–2 $\mu l$.

The test plate is mounted on support 15 by a pair of resilient members, such as elastomeric blocks 61, 62. The blocks act to bias the pads toward a non-transfer position at which the pads are spaced apart from the dispenser's sample-transfer surface, with a spacing typically of between about 0.5 to 1.0 mm.

Figure 4:
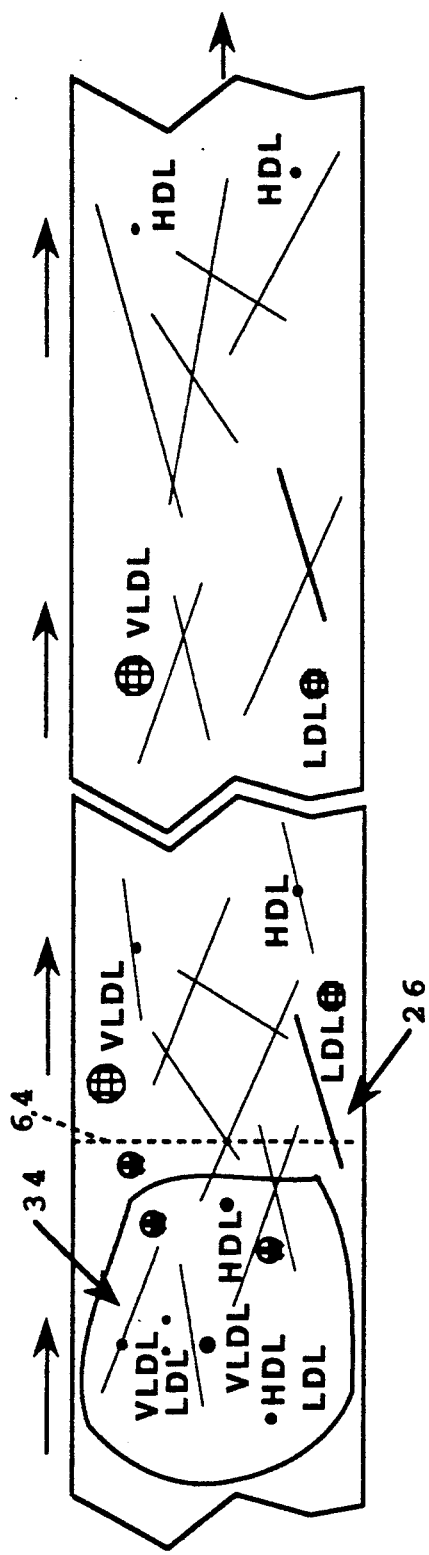
FIG. 4 illustrates the slow release of precipitating agent and precipitation of LDL and VLDL in a serum sample (left side of the figure) and the separation of HDL particles from precipitated LDL and VLDL aggregates which occurs after migration through the strip in the device (right side of the figure)

The operation of the device in an assay for determination of HDL in a small blood sample is illustrated in FIG. 4. The left portion of the figure shows the central sample-receiving region of matrix 26. The cutaway portion shows the underlying web of reservoir 34, with the web fibers coated with a slow-release deposit of precipitating agent. The right edge of the reservoir region below the matrix is indicated by dotted line 64.

Initially, a blood sample is placed in well 16 (FIG. 1), and the sample is drawn by capillarity into and through pad 22 and membrane 24, yielding a cell-free serum sample which is then drawn into matrix 26 through reservoir 34. As the sample fluid is drawn through the web in the reservoir, the precipitating agent/binder deposit on the reservoir web is slowly dissolved, releasing precipitating agent into the fluid sample. As described above, the reservoir is designed to release the entire amount of precipitating agent over a selected portion of the total solvent flow through the reservoir—typically over at least the first 10–40% of total solvent flow, and preferably at least the first 20% of flow.

As the cholesterol-containing particles in the downstream region of the solvent front are drawn into the matrix and toward the sample-collection region to the right in the figure, the aggregated and non-aggregated particles are separated chromatographically, as shown in the right in FIG. 4. The fluid sample which first reaches the sample-collection region is substantially free of non-HDL particles, but has the same HDL concentration as the cell-free (serum) sample fluid serum which is introduced into the matrix.

Figure 5:
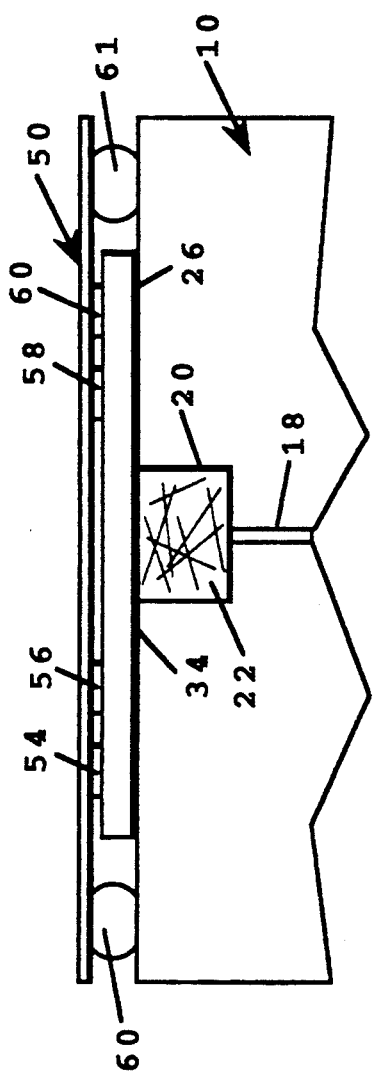
FIG. 5 is a view of the device of FIG. 1 in a sample-transfer condition.

When the serum reaches the sample-transfer sites adjacent the ends of matrix 26, the test plate is moved toward its sample-transfer position (FIG. 5), at which the pads are in contact with the matrix. At this position, sample fluid in the dispenser is drawn into the pads by capillary flow with fluid movement occurring in a direction normal to the pad surfaces. The plate is held at this position until a desired degree of wetting of the pads is achieved.

The analyte-dependent reagents in the pad produce an analyte-dependent change in the pad which can be detected optically, either visually or by a detector, in a known manner. One preferred apparatus for reading the signal levels of the pads, and for calculating a corrected analyte value based on the readings is described in co-owned U.S. patent application Ser. No. 320,474, for Controlled-Volume Assay Method and Apparatus, filed Mar. 8, 1989 now U.S. Pat. No. 5,114,350.

B. Multi-analyte Lipid Assay

This section describes embodiments of the assay device which are designed for multi-analyte determination of serum lipids, including HDL, and additionally including one or more of the following analytes: total serum cholesterol, LDL cholesterol, and serum triglycerides. As discussed above, lipoproteins can be selectively precipitated by a variety of precipitating agents, including combinations of selected polyanionic compounds and divalent cations. The use of these agents in lipoprotein s precipitation has been reviewed (Bachorik, P. S., et al., in Methods in Enzymology, Academic Press (1986), pp 78–100). The agents which have been most widely used are (a) heparin-$Mn^{2+}$ or heparin-$Ca_{2+}$, (b) dextran sulfate-$Mg^{2+}$, (c) phosphotungstate-$Mg^{2+}$, and (d) polyethyleneglycol.

The heparin agent including heparin and a divalent metal is effective at a heparin concentration of 1 mg/ml, and a concentration of up to 1 mg/ml does not precipitate HDL. $Mn^{2+}$, typically in the form of the $MnCl_2$ salt, should be at least about 0.04 M for complete precipitation of non-HDL (apoB-containing) lipoproteins, and preferably between about 0.006 and 0.092 M $Mn^{2+}$. Similar concentrations of $Ca^{2+}$, can be substituted for $Mg^{2+}$.

The dextran sulfate agent including dextran sulfate and $Mg^{2+}$ preferably employs dextran sulfate of molecular weight about 50 kd (kilodaltons). At higher molecular weights e.g., 500 kd, a significant amount of HDL is precipitated. At lower molecular weights, e.g., 15 kd, the apoB lipoproteins are incompletely precipitated. The optimal dextran sulfate concentration for selectively precipitation of non-HDL particles is about 0.91 mg/ml, and concentration up to 10 mg/ml do not precipitate HDL. The concentration of $Mg^{2+}$, typically in the form of $MgCl_2$, is between about 0.045 and 0.15 M.

The phosphotungstate reagent includes a water-soluble phosphotungstate and $Mg^{2+}$, typically in the form of $MgCl_2$. Concentrations of the agent effective to selectively precipitate non-HDL lipoproteins are between 2–8 mg/ml of phosphotungstate and between about 0.025 and 0.075 M Mg salt.

The precipitating agent is typically formulated in aqueous buffer, such as Tris-HCl buffer (phosphate buffer is preferably avoided) to a desired concentration which allows infusion of the reservoir web with a selected amount of precipitating agent. The total amount of agent in the reservoir is calculated from the estimated solvent-front volume in the assay device which will contain precipitating agent, at the desired concentration of precipitating agent, and the total amount of precipitating agent required to produce that concentration. The formulation applied to the web may include a binder, as described with reference to FIG. 3a, or precipitating agent alone, which is coated with a slow-release coating. Details of a reservoir containing a dextran sulfate-$MgCl_2$ precipitating agent are given in Example 1.

FIG. 6 is a plan view of the upper surface of matrix 26 in device 14, as viewed through support 50, also showing the four reaction pads carried on the plate, and indicated at 54, 56, 58, and 60. The dotted lines 66 in the figure indicate the edges of region 22 and approximately the edges of reservoir 34 in the device, shown in cutaway below matrix 26. The reservoir is designed for slow release of dextran sulfate and $Mg^{2+}$, as described above. It will be appreciated from the figure that sample fluid being drawn toward both sides of the matrix is exposed to precipitating agent, so that non-HDL particles on both sides of the matrix are separated from HDL analyte when the sample fluid reaches the sample-collection regions underlying the reaction pads.

Two of the reaction pads in the FIG. 6 embodiment are designed for duplicate assay of HDL cholesterol (HDL). Two reference standard pads, (Blank), provide a self-correcting standard curve for determining cholesterol values, as described in U.S. patent application Ser. No. 396,326, for "Self-Corrected Assay and Method", filed Aug. 23, 1989.

Each of the test pads contains common-pathway reagent components for converting $H_2O_2$ to a colored signal reaction product. The common-pathway components include peroxidase, and a dye (meaning a single dye or coupled dye system) which is converted by the peroxidase, in the presence of $H_2O_2$, to a distinctively colored signal reaction product. Enzymatic color reactions which employ a variety of substrate-specific oxidases, for enzymatic generation of $H_2O_2$ and subsequent oxidation of a dye to form a colored reaction product are well known.

The HDL pads contain, in addition to the common-pathway components, cholesterol esterase for releasing free cholesterol from lipoproteins, i.e., HDL, and cholesterol oxidase, for producing $H_2O_2$ by reaction with free cholesterol in the sample fluid.

The two reference standard pads contain, in addition to the common-pathway components, different known amounts of a non-cholesterol reference compound, preferably a D-amino acid, and an oxidase, such as D-amino acid oxidase, for generating $H_2O_2$ when the pad is wet with sample fluid.

The reaction components present in the four reaction pads are summarized in Table 1.

TABLE I

| Components | Pad Reference | HDL |
| --- | --- | --- |
| Sample (HDL) | + | + |
| cholesterol esterase | | + |
| cholesterol oxidas | | + |
| D-amino acid | + | |
| D-amino acid oxidase | + | |
| peroxidase + dye(s) | + | + |

In the above assay device, the amount of reference compound added to each reference standard is selected to produce, in the presence of a given volume of defined reaction mixture, a signal level corresponding to a known concentration of cholesterol, assayed under identical conditions in the presence of cholesterol oxidase. The actual reference standard produced in the assay will also depend on (a) the amount of soluble interfering compounds present in the serum sample (as distinguished from non-HDL compounds which interfere with the measurement of HDL cholesterol), (b) the condition of the reaction components in the pad, including the activity of the common-pathway components and (c) reaction conditions, including temperature and reaction time.

Figure 8:
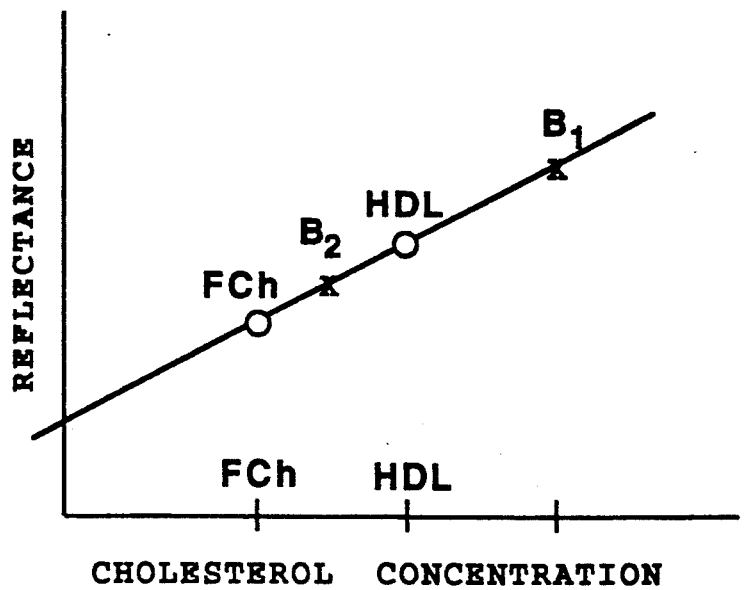
FIG. 8 is a plot illustrating the determination of HDL and total cholesterol values from the assay device shown in FIG. 6.

The signal values of the two pads, when plotted as a function of reference compound concentration, gives a two-point standard curve such as the one shown in FIG. 8. The signal value is calculated from reflectance or other measured signal properties using known relationships between the measured signal property and plotted signal value. The fact that the curve in FIG. 8 does not cross the origin of the graph indicates non-linear inhibition effects.

The signal values measured for the duplicate HDL pads are plotted on the standard curve, and the known correspondence between reference standard and cholesterol concentrations is used to determine the cholesterol concentration in each of these pads. It will be appreciated that the cholesterol values so calculated are (a) calculated on the basis of a standard curve, and (b) self-corrected for variations in reaction conditions, and for inhibitory effects and loss of activity of common-pathway components, assuming that all four reaction pads are subject to the same variations in these factors. The concentration of cholesterol associated with HDL can be calculated from the average in cholesterol concentration determined from the two HDL sample pads.

FIG. 7 is a plan view of the upper surface of a matrix 66 in an assay device 68, where the dotted lines again indicate the edges of the pad region underlying the matrix. As indicated, reservoir 72 in this device extends over the right half of the pad region only, and accordingly, the sample fluid which is drawn toward the right side of matrix 66 in the figure passes through the reservoir, causing a slow release of precipitating agent and precipitation of non-HDL lipoproteins in the sample material. The material flowing from the pad toward the left side of the matrix is not exposed to precipitating agent.

The four reaction pads in the FIG. 7 embodiment are designed for measuring total cholesterol (TCh), triglyceride lipid (TG), and HDL cholesterol (HDL), and include a reference standard correction pad (Blank) for correcting the other three readings. Each pad contains the above-described common pathway components for converting $H_2O_2$ to a distinctly colored signal reaction product. The reference standard pad contains a known amount of reference compound, such as D-amino acid, and a corresponding oxidase, as described above.

The total cholesterol and HDL test pads each include, in addition to the common pathway components, cholesterol esterase, for releasing esterified cholesterol in free-cholesterol form from serum lipoproteins, including HDL, LDL, and VLDL particles, and cholesterol oxidase, for producing $H_2O_2$ by reaction of with free cholesterol in the sample fluid.

The triglyceride pad includes, in addition to the common-pathway components, lipase, L-glycerol kinase, and L-glycerol-3-phosphate oxidase, for generating $H_2O_2$ from triglyceride. These three enzymes function to convert the triglyceride substrate into L-glycerol-3-phosphate, and to oxidize the latter compound, with generation of $H_2O_2$. Since the serum sample drawn into the TG pad contains all of the serum lipoproteins, the TG signal represents total serum triglycerides.

Figure 9:
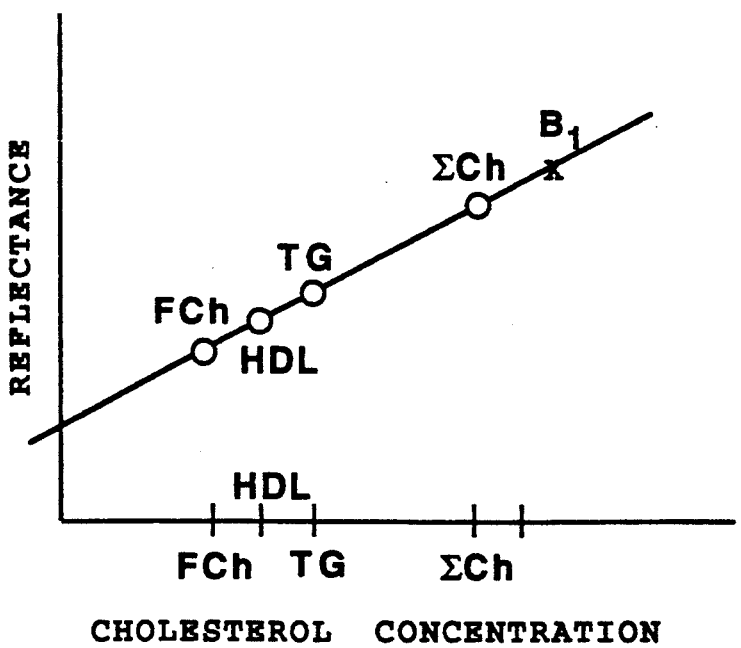
FIG. 9 is a plot illustrating the determination of total cholesterol, HDL, total cholesterol, and serum triglyceride from the assay device in FIG. 7.

The standard reference pad in the assay is used to construct a single-point standard curve such as shown in FIG. 9. The standard curve corresponds to predetermined concentrations of cholesterol and triglyceride, and thus provides a plot for determining analyte concentrations from measured signal values. As described above, the standard curve also functions to correct analyte readings for loss of enzyme activity in the common-pathway components, and for variations in reaction conditions, although non-linear inhibition effects are uncorrected. A two-point standard curve, such as shown in FIG. 7, could of course be constructed using a five-pad assay device.

The signal values for total cholesterol, triglyceride, and HDL are plotted on the standard curve to determine self-corrected analyte concentration values for the three analyte pads. From these values, LDL cholesterol can then be calculated from the relationship:

LDL cholesterol = total cholesterol
- total triglycerides/5 - HDL cholesterol.

From the foregoing it will be appreciated how various objects and features of the invention are met. The assay device provides a simple one-step method for assaying an analyte in a fluid sample containing a selectively precipitable interfering compound, without the need to pretreat or centrifuge the sample fluid. This feature is particularly useful for assaying multiple analytes in small volumes which cannot practically be pretreated to remove interfering compounds. In particular, the method allows a small blood volume, typically less than 50 μl, to be employed in multi-analyte assays in which at least one analyte, e.g., HDL, requires the selective removal of related lipoproteins.

The following example illustrate the preparation and use of assay devices for cholesterol and other lipid testing. The examples are intended to illustrates, but not limit the scope of the invention.

EXAMPLE 1

Assay for HDL

An assay device like that described in FIG. 1 was prepared using the preferred filter materials described in Section A. Stock solution A contained 2 g/100 ml 50,000 dalton dextran sulfate and 1 g/100 ml of gelatin. Stock solution B contained 1 M Mg acetate. To a ⅛" by 5/16" by 150 micron thick glass fiber filter was added 0.75 μl each of stock solutions A and B and 2.21 μl water. The pad was dried for 20 minutes at 50° C. and assembled into the device, as described above.

Four reaction pads in the device contain the reagents described with respect to FIG. 6. Each reaction pad was prepared from a 150 micron thick paper filter obtained from Schleicher and Schull, and cut into 2×4 mm rectangles. The two reaction pads for cholesterol determination were infused with 10 μl of a reagent solution containing 150 U/ml cholesterol ester hydrolase, 10 U/ml cholesterol oxidase, 80 U/ml peroxidase, and 20 mM 4-aminoantipyrine (4-AAP) and 80 mM N-ethyl-N-sulfohydroxypropyl-m-toluidine (TOOS), in reduced form, in deionized water. The two reaction pads for the reference standards contain a layer infused with 40 U/ml D-amino acid oxidase, 80 U/ml peroxidase, and 20 mM 4-aminoantipyrine (4-AAP) and 80 mM TOOS, in reduced form, in deionized water, then dried. Next, 3 μl of 20 mM D-amino acid in ethanol is added and dried. The amounts of reference standard are calibrated, in a liquid-phase assay containing a defined reaction buffer, and under defined reaction conditions, and matched with similarly measured cholesterol concentrations from a predetermined volume of known-concentration solution of cholesterol in non-ionic detergent. After drying under reduced pressure, the reaction pads are assembled and attached to the reaction pad plate in the device.

A whole blood sample from a human test subject is obtained conventionally, and applied to the strip in an amount sufficient to wet the three reaction zones on the strip. The strip is incubated at room temperature for 90 seconds, or until no further color development is observed.

The analyte-related signal is read by reflectance spectrophotometry, at an illuminating wavelength of 500 nm. The values for the reference standard pads are plotted to give a two-point self-corrected standard curve from which the cholesterol readings were calculated.

EXAMPLE 2

Serum Lipids Assay

The assay device is similar to that described with reference to FIG. 7, and is prepared using the reservoir and reaction pad formulations described in Example 1.

The values for the five reaction pads are measured at 500 nm as above. The reflectance measurement from the fifth pad is used to construct a standard curve, and this curve is standardized to known cholesterol and triglyceride concentrations as described in Example 1. The signal values from the first four pads are plotted on this curve, and the corrected analyte concentration is read from the corresponding position on the concentration axis.

Total serum cholesterol, HDL, free cholesterol and triglycerides are determined from the standard curve, and these values are used to calculate LDL, as described above.

Although the invention has been described with reference to particular embodiments and configurations, it will be appreciated by one skilled in the art that various changes and modifications may be made without departing from the invention. Specifically, the release of precipitate at a rate which produces a selected concentrating of the agent in the matrix.

It is claimed:

1. An assay device for measuring high density lipoprotein (HDL) in a fluid sample which also contains low density lipoproteins (LDL) and very low density lipoproteins (VLDL) comprising a sieving matrix capable of chromatographically separating aggregated and non-aggregated lipoproteins, as such fluid sample flows through the matrix from a sample-application site to a sample-collection site in the matrix, a reagent reservoir which includes an LDL- and VLDL-precipitating agent, effective, within a predetermined concentration range, to selectively aggregate LDL and VLDL, and release means in contact with the matrix for producing a rate of release of said agent from the reservoir into the matrix, as fluid flowing through the matrix is brought into contact with the matrix, adjacent said sample-application site, which is effective to produce a concentration of the agent in the sample fluid which is within such predetermined concentration range, and an assay pad in which HDL present in fluid sample collected at the sample-collection site can be assayed.

2. The device of claim 1, wherein the matrix is composed of a network of fibers, and the LDL- and VLDL-precipitating agent and release means comprising the reagent reservoir are coated on the fibers.

3. The device of claim 2, wherein the reagent reservoir is composed of an LDL- and VLDL-precipitating agent mixed with a water-soluble binder which forms the release means in the reservoir.

4. The device of claim 3, wherein the binder is a water-soluble polymer selected from the group consisting of gelatin, agarose, agar, polyoxides, polypropylene oxides, polyethylene imines, polyacrylic acid, polyacrylamide, polymethacrylamide, polymethacrylic acid, polyvinylacetate, polyvinylpyrrolidone, polyvinyloxazolidone, and water-soluble cellulose compounds.

5. The device of claim 2, wherein the release means in the reservoir includes a water-soluble polymer coating which covers the precipitating agent.

6. The device of claim 1, for use in measuring serum cholesterol associated specifically with high-density lipoproteins, wherein the LDL- and VLDL-precipitating reagent includes a polyanionic compound and a group II metal cation selected from the group consisting of $Mg^{2+}$, $Mn^{2+}$, and $Ca^{2+}$, and the release means is effective to release the polyanionic compound, on contact with sample fluid, at a rate which produces a concentration of the compound effective to selectively aggregate very-low density lipoproteins, and low-density lipoproteins.

7. The device of claim 6, wherein the polyanionic compound is selected from the group consisting of sulfated polysaccharides, heparin, and phosphotungstic acid.

8. The device of claim 7, wherein the polyanionic compound is dextran sulfate, the group II metal is $Mg^{2+}$, and the concentration of the precipitating reagents in the matrix, after contact with the fluid sample, is between about 0.5 and 1.0 mg/ml for dextran sulfate and between about 0.045 to 0.15 M $Mg^{2+}$.

9. The device of claim 1, for determination of serum high-density lipoprotein, wherein the assay pad includes cholesterol esterase, cholesterol oxidase, a peroxidase and a reduced dye which produces a detectable color change when oxidized in the presence of $H_2O_2$ and the perioxidase.

10. An assay device for measuring serum cholesterol associated with high-density lipoproteins in a blood or serum sample, comprising a sieving matrix capable of chromatographically separating aggregated from non-aggregated material in such sample, as the sample flows through the matrix from a sample-application site to a sample-collection site on the matrix, a reservoir which includes a polyanionic reagent effective, within a selected concentration range and in the presence of a group-II metal cation, to selectively aggregate low-density lipoproteins and very low-density lipoproteins in serum, and release means in contact with the matrix for limiting the rate of release of the reagent from the reservoir into the matrix, as fluid flowing through the matrix is brought into contact with the matrix, to produce a reagent concentration within said selected range, wherein low-density lipoproteins and very-low-density lipoproteins in the fluid are selectively aggregated and separated from high-density lipoproteins as the sample fluid flows toward the sample-collection site, and an assay pad to which fluid sample collected at the sample-collections site can be transferred, and including cholesterol esterase, cholesterol oxidase, a perioxidase and a reduced dye which produces a detectable color change when oxidized in the presence of $H_2O_2$ and the perioxidase.

11. The device of claim 10, wherein the matrix is composed of a network of fibers, and the LDL- and VLDL-precipitating agent and release means comprising the reagent reservoir are coated on the fibers.

12. The device of claim 11, wherein the release means is a water-soluble binder.

13. The device of claim 12, wherein the binder is a water-soluble polymer selected from the group consisting of gelatin, agarose, agar, polyoxides, polypropylene oxides, polyethylene imines, polyacrylic acid, polyacryaminde, polymethacrylamide, polymethacrylic acid, polyvinylacetate, polyvinylpyrrolidone, polyvinyloxazolidone, and water-soluble cellulose compounds.

14. The device of claim 11, wherein the release means in the reservoir includes a water-soluble polymer coating which covers the precipitating agent.

* * * * *